United States Patent [19]

van Duijn

[11] 4,192,250

[45] Mar. 11, 1980

[54] VALVE-CENTRIFUGE

[76] Inventor: Pieter van Duijn, Rhijngeesterstraatweg 110, Oegstgeest, Netherlands

[21] Appl. No.: 856,406

[22] Filed: Dec. 1, 1977

[30] Foreign Application Priority Data

Dec. 9, 1976 [NL] Netherlands ............... 7613690

[51] Int. Cl.² ............... B04B 5/12; B05C 11/08; G01N 33/16
[52] U.S. Cl. ............... 118/52; 422/72; 233/20 R; 233/26
[58] Field of Search ............... 233/20 R, 26; 118/52; 23/259; 422/72

[56] References Cited

U.S. PATENT DOCUMENTS

| | | | |
|---|---|---|---|
| 3,352,280 | 11/1967 | Hughes et al. | 118/319 X |
| 3,619,865 | 11/1971 | Hazzard | 118/52 X |
| 3,856,470 | 12/1974 | Cullis | 23/259 X |
| 3,870,789 | 3/1975 | Mikat | 233/26 X |
| 3,880,592 | 4/1975 | Kelley et al. | 422/72 |
| 3,899,296 | 8/1975 | Mailen et al. | 233/26 X |
| 3,906,890 | 9/1975 | Amos et al. | 118/52 X |
| 4,031,852 | 6/1977 | Clarke et al. | 118/52 |
| 4,035,156 | 7/1977 | Shumare | 233/26 X |

OTHER PUBLICATIONS

G.I.T. Fachzeitschrift fuer des Laboratorium, vol. 15, No. 1, Jan. 1971.

*Primary Examiner*—Michael S. Marcus

[57] ABSTRACT

Centrifuge for depositing cytological material from a suspension onto a substrate, such as a slide, comprising a rotor having recessed therein a plurality of sedimentation chambers each providing a location for a substrate, said rotor further comprising for each sedimentation chamber a drainage channel leading from the bottom of the chamber to the periphery of the rotor, and a valve normally sealing said drainage channel, the drainage channel being constricted such that when the valve is enabled the fluid flow through the drainage channel is limited up to a predetermined maximum.

5 Claims, 2 Drawing Figures

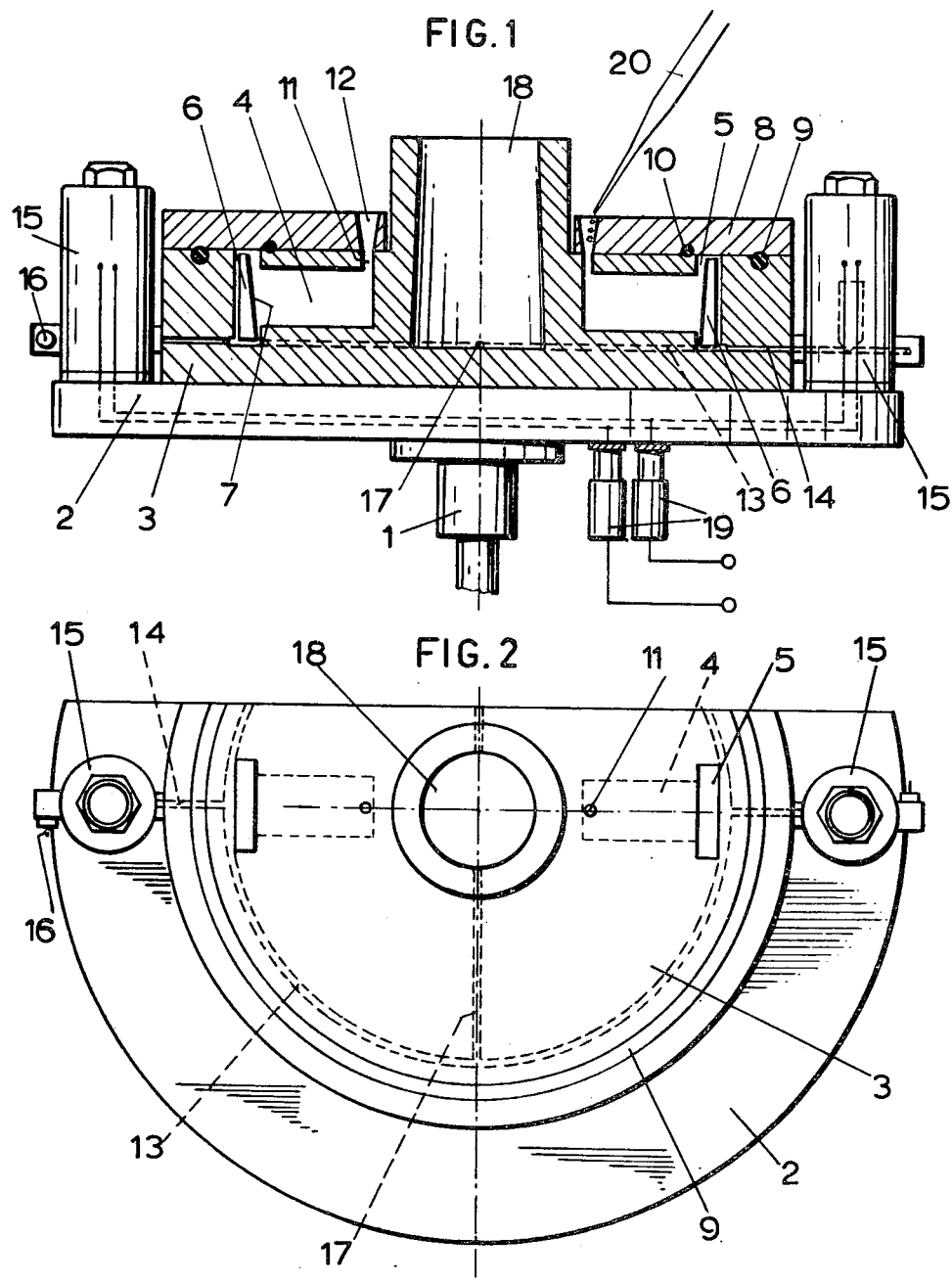

VALVE-CENTRIFUGE

The invention relates to a novel centrifuge to be used to sediment on a small glass plate such as a microscope slide, or a microscope cover slip, cells and similar particles from a suspension, in order to enable a cytological and cytochemical examination of such cells, comprising a rotor with a number of radially extending sedimentation chambers, each of said chambers being provided with means to support a small glass plate in an essentially tangential position at the side most distant from the rotor axis, and with a liquid access aperture at the side nearest to the rotor axis.

A similar centrifuge is known, in which, while the cells are sedimenting on the glass plate, the suspending liquid is absorbed by a ring of filter paper, to be positioned on the glass plate for this purpose.

Preparations made with such centrifuges, prove unsatisfactory to meet the more exacting demands which presently have to be made in view of the trend towards more quantitative cytological and cytochemical examinations. Using such centrifuges there is a great loss of cells, and because of the magnitude of this loss depends both on the concentration of the cells in the suspension, and the nature of the cells, the loss factor is variable as well as unknown, while simultaneously a certain selection occurs. The result is that the sediment obtained, does not render a proportional image of the totality of the cells present in the suspension liquid and is unsuitable for quantitative examination.

The object of the invention is to provide a centrifuge with which preparations can be made, which are to a high degree proportional to the contents of the suspension, and which therefore meet the present high requirements. To this purpose the invention is distinguished by having situated in each sedimentation chamber at the end most distant from the rotor axis, a drainage channel leading to a drainage aperture situated at a further distance from the rotor axis and that in this channel there has been incorporated a valve which can be operated while the rotor rotates.

With the centrifuge according to the invention it is possible to first centrifuge during a certain period and to sediment the cells without draining the suspension liquid, and only after a sediment has formed on the glass plate, to open the valves and remove the liquid. The result of this procedure is an only minute loss in cells, which moreover proves to be proportional and therefore does not constitute an objectionable factor for quantitative studies.

The preparations obtained are highly uniformly spread and do not show any meaningful differences between their pheripheral and central parts.

For a good quality of the preparations, the suspension liquid should not be drained too fast; excessive drainage rates, lead to cell loss and cell damage, especially at the periphery of the preparations. In connection herewith, the invention is further distinguished by incorporating in the drainage channel a constriction limiting the drainage speed.

Preferentially this constriction should be chosen in such a way as to limit the rate of drainage during centrifugation to at most 100 ml suspension liquid per minute from each sedimentation chamber.

It was found, that optimal results were obtained with a drainage rate that would drain a sedimentation chamber over a period between 5 and 15 minutes.

Lower drainage speeds give no noticeably improved results and result only in needless loss of time.

Special possibilities are created for cell-research when the centrifuge according to the invention is further distinguished by the provision of a central reservoir, with which each sedimentation chamber is connected via a channel.

By providing, during centrifugation and after the suspension liquid has been drained and the valves have been closed, a fixation fluid to the said sedimentation chambers from said central reservoir, one fixes the cells on the glass plates in their actual, through centrifugation, flattened state.

With this procedure preparations are obtained in which the interior of the cells can be observed with an exceptional clarity and detail and which therefore offers heretofore unknown possibilities for, among others, cytophotometric and morphometric determinations. It was further shown that the cells were flattened to a practically uniform thickness, allowing the determination of the cell volumes through measurement of surface areas.

With the centrifuge according to the invention, it is possible not only to subject the preparations to a fixation process, but also to treat them with other fluids, such as those for coloring different components of the cells. Such a sequence of treatments can be fairly simply automated by extending the centrifuge with a programmable function controller, which opens and closes the valves and regulates the supply of fluids to the central reservoir in the required sequence. An instrument is then obtained that is eminently suitable for clinical use, where it can provide a substantial saving of labor when used for more or less identical investigations.

The centrifuge according to the invention is further distinguished by having the place where a supply channel enters the sedimentation chamber situated preferentially at least as far from the rotor axis as the glass plate placed in said chamber.

The effect thereof is, that the fluid which is fed to the sedimentation chamber during centrifugation will not create a strong current over, or along this glass on which the cells have been sedimented, but will flow gradually from the sides over the glass without damaging or removing the cells on it.

The invention is further explained by a drawing in which an example of an embodiment of a centrifuge according to the invention is shown.

In this drawing:

FIG. 1 represents a cross section and

FIG. 2 a top view of the rotor of the centrifuge.

On the vertical axis 1, driven by the motor (not shown), is situated a disc 2, on which the rotor body 3 is mounted. In this rotor body 3 a number of sedimentation chambers 4 have been made. The drawing shows two of such chambers; however a greater number, for instance eight, or six of such chambers 4 can be situated in such a body 3.

Each sedimentation chamber 4 has on the upper side an oblong aperture 5, under which a holder 6 with a glass plate 7 can be placed in the chamber 4. The apertures 5 are closed with the common cover plate 8, which is fastened with bolts (not shown) onto the rotor body 3. The sealing rings 9 and 10 ensure a leaktight closure of the aperture 5.

Each chamber 4 has on its side nearest to the centre of the rotor a small aperture 11, which relates to the aperture 12 in the coverplate 8.

The sedimentation chambers 4 are interconnected at their side nearest to the circumference of the rotation body 3 through the circulation channel 13. The chambers 4 and the channel 13 are also connected with the two radial channels 14. These each lead through the electromagnetic valves 15, mounted on the disc 2, and terminate in the narrow tubes 16 forming a drainage aperture. The tubes 16 have an interior diameter of 0.1 mm and are constricted experimentally till they each have the required flow resistance.

The two radial channels 17 connect the circulation channel 13 with the central reservoir 18, which has a slighty conical shape, widening downwards. Channels 13 and 17 form a supply channel for introduction of a fixative or other fluid from central reservoir 18 to sedimentation chambers 4 as described below.

The magnet coils of the valves 5 are connected with sliprings and slipcontacts 19; by connecting these slipcontacts in turn to a suitable source of electrical power, the valve 15 can be opened or closed at will.

The use of the above centrifuge is as follows: After removal of the coverplate 8 from the rotorbody 3, the holders 6 with the glass plates 7 are placed in the sedimentation chambers 4 and these chambers 4 are filled with sedimentation fluid. The coverplate 8 is now mounted, after which the centrifuge is run for a few seconds to expel possible air inclusions from the chambers 4.

A small, measured amount of the cell suspension contained in a tube 20 is then introduced in the chambers 4, through the apertures 12 and 11, and the apertures 12 are closed with a stopper or screw, which is provided with a small hole, directed towards the centre of the centrifuge, of which the function is to prevent vacuum from developing in the chambers 4 during centrifugation.

After centrifugation for 5 minutes at a centripetal acceleration of approximately 80 g, the valves 15 are actuated by means of the slipcontacts 19 and the sedimentation fluid commences to drain from the tubes 16. After 5 to 15 minutes all fluid is drained. To facilitate complete drainage of the fluid, the holders 6 are slightly inclined, so that the glass plates 7 are placed under an angle of 4° to 6° with regards to the rotation axis and no fluid remains on the glass plates 7.

Now, under continuing centrifugation, the valves 15 are closed, by deenergising them and by means of the central reservoir 18, the channels 17 and the circulation channel 13 a fixative fluid is introduced into the sedimentaton chambers 4. This fluid flows into the chambers 4 from behind the glass plates 7 and therefore cannot damage the sedimented cells. After the required treatment period, the fixative fluid is removed from the chambers 4, by opening the valves 15.

In a similar manner, the cells on the glass plates 7 can be subjected to one or more further treatments.

After drainage of the last fluid, the centrifuge is stopped, the coverplate 8 is removed and the glass plates 7 with the sedimented and treated cells are taken from the chambers 4 as prepared microscope slides. They are now ready for examination.

What is claimed is:

1. Centrifuge apparatus to sediment cells or similar particles from a suspension onto glass plates for cytological or cytochemical examination of such cells or particles, said apparatus comprising a rotor member for rotation about an axis having a plurality of radially extending sedimentation chambers, each of said chambers provided near the side most distant from the rotor axis with means to support a removeable glass plate in an essentially tangential position, each of said sedimentation chambers provided at the side nearest to the rotor axis with a fluid access aperture, characterized in that each sedimentation chamber comprises drainage channel means leading radially outward from the side of said sedimentation chamber most distant from the rotor axis, said drainage channel means including drainage aperture means situated at a further distance from the rotor axis and valve means disposed between said drainage channel means and said drainage aperture, said valve means adapted for operation during the rotation of said rotor member.

2. Apparatus according to claim 1, characterized in that the drainage channel means comprises a fixed constriction limiting the drain velocity.

3. Apparatus according to claim 2, characterized in that the constriction in the drainage channel is selected to restrict the drainage rate from each sedimentation chamber in such a manner that at most 100 ml suspension liquid per minute can be drained from each sedimentation chamber.

4. Apparatus according to claim 2, characterized in that a central reservoir is incorporated in the rotor, each sedimentation chamber being connected to said central reservoir by means of a supply channel.

5. Apparatus according to claim 4, characterized in that the entry of the supply channel into the sedimentation chamber is situated in a position which is at least as far distant from the rotor axis as the glass plate support means placed in this chamber.

* * * * *